US00PP31427P2

(12) United States Plant Patent
Slaughter et al.

(10) Patent No.: US PP31,427 P2
(45) Date of Patent: Feb. 4, 2020

(54) NECTARINE TREE NAMED,'WANECTONE'

(50) Latin Name: *Prunus persica nucipersica*
Varietal Denomination: Wanectone

(71) Applicant: Wawona Packing Co., LLC, Cutler, CA (US)

(72) Inventors: John Keith Slaughter, Fresno, CA (US); Kaylan M. Roberts, Fresno, CA (US)

(73) Assignee: Wawona Packing Co., LLC, Cutler, CA (US)

( * ) Notice: Subject to any disclaimer, the term of this patent is extended or adjusted under 35 U.S.C. 154(b) by 0 days.

(21) Appl. No.: 16/350,445

(22) Filed: Nov. 15, 2018

(51) Int. Cl.
*A01H 5/08* (2018.01)
*A01H 6/74* (2018.01)

(52) U.S. Cl.
USPC ..... Plt./189
CPC ..... *A01H 6/7454* (2018.05)

(58) Field of Classification Search
USPC ..... Plt./189
See application file for complete search history.

(56) References Cited

U.S. PATENT DOCUMENTS

PP14,242 P2 10/2003 Bradford

*Primary Examiner* — Anne Marie Grunberg
(74) *Attorney, Agent, or Firm* — Potter Anderson and Corroon LLP

(57) ABSTRACT

A new and distinct variety of nectarine tree (*Prunus persica nucipersica*), which is denominated varietally as 'Wanectone', and which produces an attractively colored white-fleshed, freestone nectarines which is mature for harvesting and shipment approximately June 20 to June 29 under the ecological conditions prevailing in the San Joaquin Valley of central California.

4 Drawing Sheets

Botanical designation: *Prunus persica nucipersica.*
Varietal denomination: 'Wanectone'.

BACKGROUND OF THE NEW VARIETY

The present variety of nectarine tree resulted from an on-going program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross pollinations each year to produce seedling populations from which improved progenies are evaluated and selected.

The seedling, 'Wanectone' was originated by the breeders at Wawona Packing Company and selected from a population of seedlings growing in our experimental orchards which are located near Fowler, Calif. The seedlings, grown on their own roots, were derived from planting seed of a Wawona Packing Company seedling, 'N21.066', an unpatented nectarine seedling used as the female parent. The pollen parent of this seedling was from an unpatented nectarine Wawona Packing Company seedling, 'N21.079'. The resulting fruit was collected from the female parent at a mature stage and seeds were extracted in August of 2009. After a period of stratification, the seed was placed in the greenhouse by population, and then field planted for tree establishment, and ultimately to exhibit fruit for evaluation. One white-fleshed nectarine seedling, which is the present variety, exhibited especially desirable characteristics, and was then designated as 'H5.095'. This seedling was marked for subsequent observation. After the 2013 fruiting season, the new variety of nectarine tree was selected for advanced evaluation and repropagation.

ASEXUAL REPRODUCTION

Asexual reproduction of this new and distinct variety of nectarine tree was accomplished by budding the new nectarine tree onto 30 trees of 'Nemaguard' Rootstock (unpatented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Wanectone' is a new and distinct variety of nectarine tree, which is considered of relatively large size, and which has a vigorous growth characteristic. This new tree is also a regular and productive bearer of relatively large, firm, white-fleshed, low acid fleshed freestone fruit which have a very good flavor and eating qualities.

This new nectarine tree has a medium chilling requirement of approximately 500 hours, and further produces relatively uniformly sized fruit throughout the tree's canopy. In addition to the foregoing, the fruit of the new nectarine also appears to have good handling and shipping qualities. The 'Wanectone' Nectarine tree bears fruit which are typically ripe for commercial harvesting and shipment on approximately June 20 to June 29 under the ecological conditions prevailing in the San Joaquin Valley of central California. In relative comparison to the 'Diamond Pearl' nectarine tree (U.S. Pat. No. 14,242), which is the closest known variety, the current variety of nectarine tree bears fruit that is freestone and the comparator variety produces fruit that is clingstone. The current variety ripens approximately 1 week later than the 'Diamond Pearl' (U.S. Pat. No. 14,242) nectarine tree, used as the commercial comparative variety. Further, the current variety produces fruit that is approximately 7.0 millimeters larger when grown under the same conditions and fruit numbers per tree. In relative comparison to the 'N21.066' seed parent tree, the current variety is contrasted by ripening approximately 7 days later when compared to the seed parent. In comparing the current variety to its unpatented 'N21.079' nectarine pollen parent the current variety is white-fleshed. Further the current variety ripens approximately 15 days after the 'N21.079' pollen parent.

Figure 1:
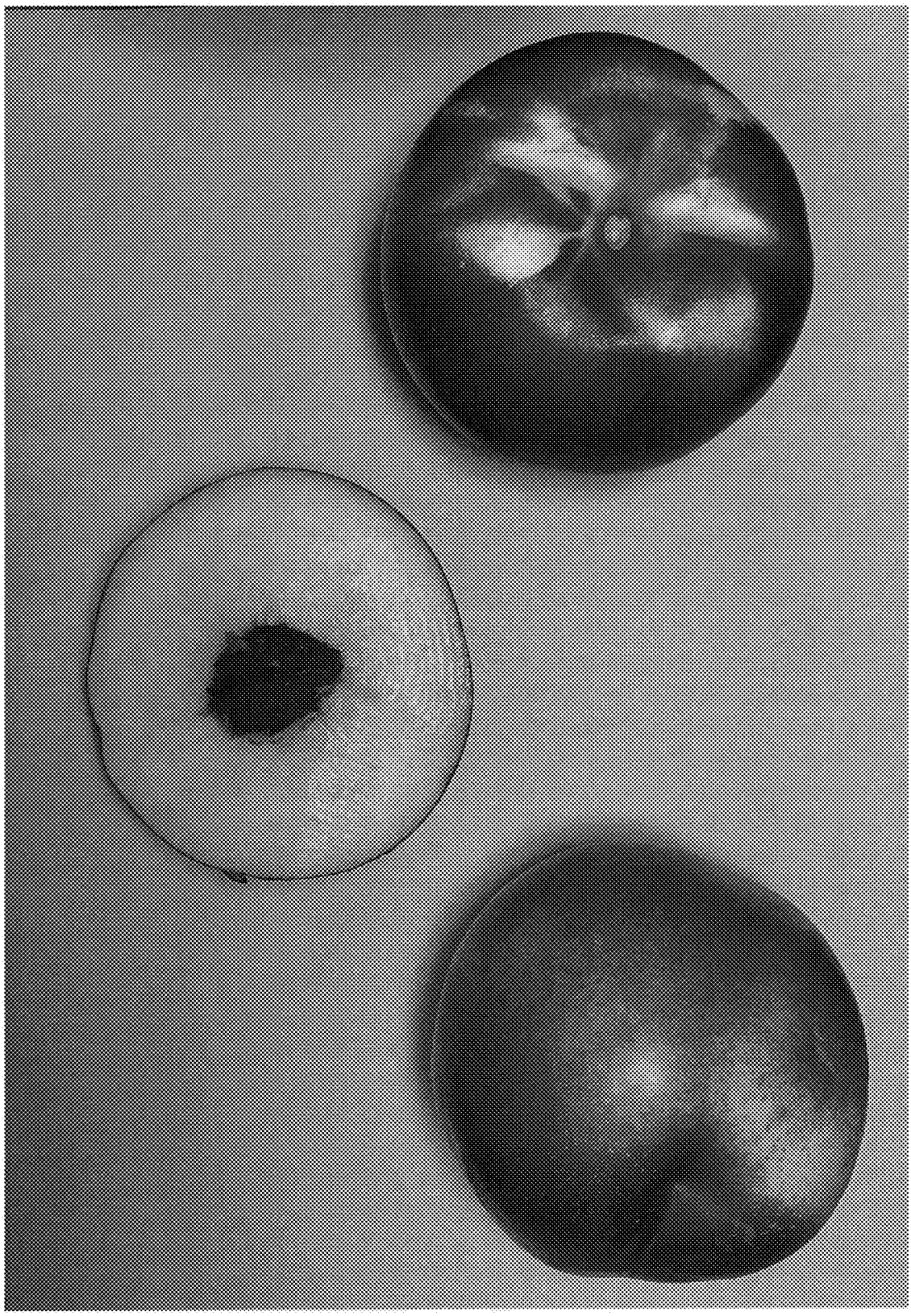
FIG. 1 is a color photograph of two whole mature fruit harvested, from a fifth leaf year tree, displaying both the apical and basal fruit aspects. In addition to the whole mature fruit, the photograph displays one mature fruit bisected transversely through the equatorial plane revealing the flesh color and stone characteristics thereof. The external coloration of the fruit as shown in the photograph is sufficiently matured for harvesting and shipment.
Figure 2:
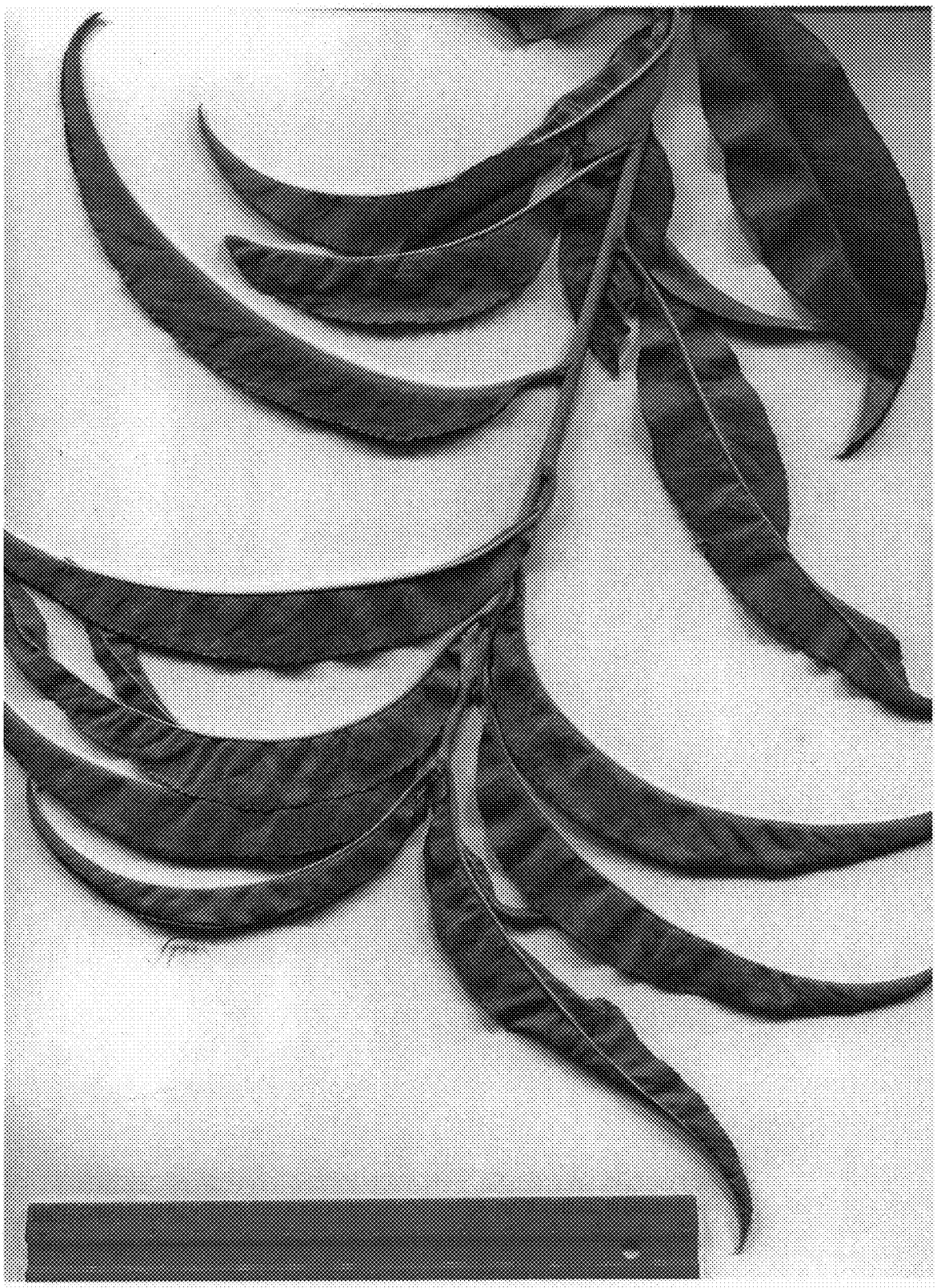
FIG. 2 is a color photograph of a branch and leaves taken from a seventh leaf year tree.
Figure 3:
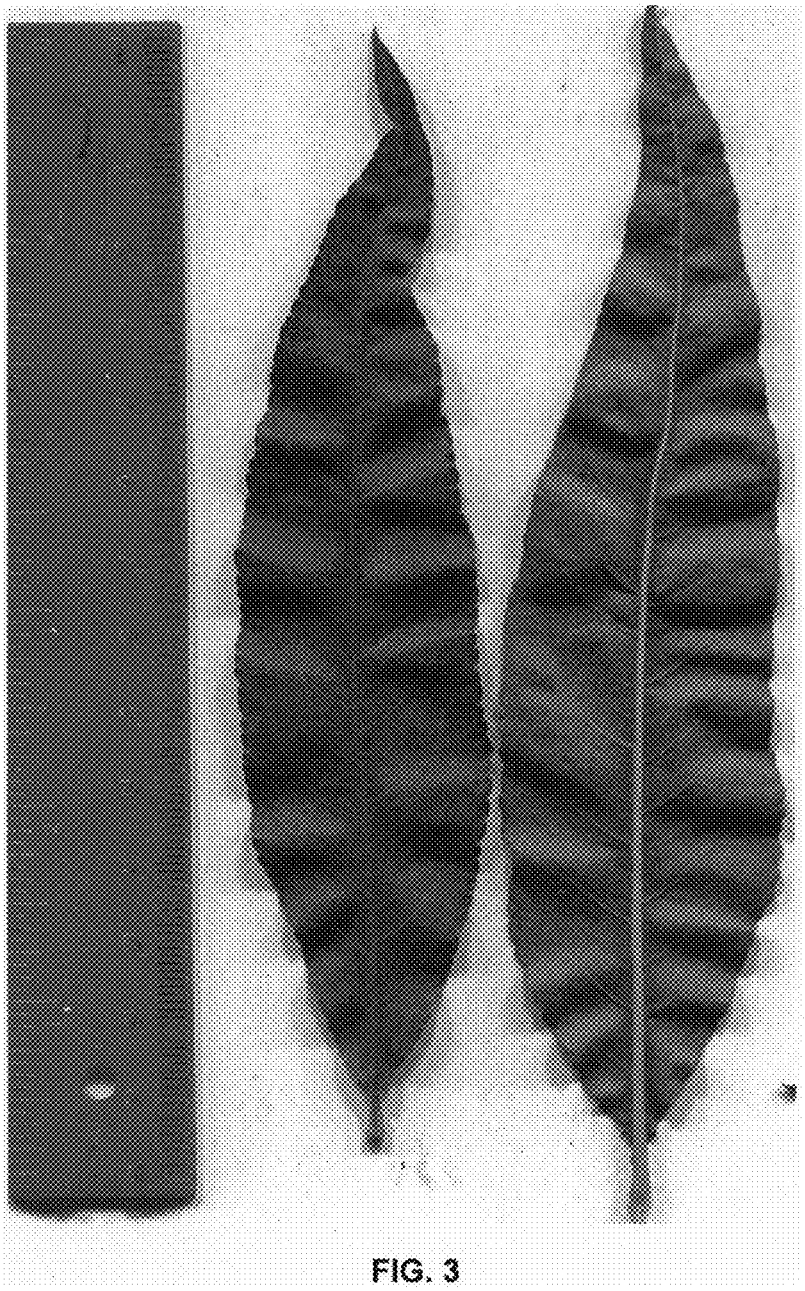
FIG. 3 is a color photograph of leaves from a seventh leaf year tree.
Figure 4:
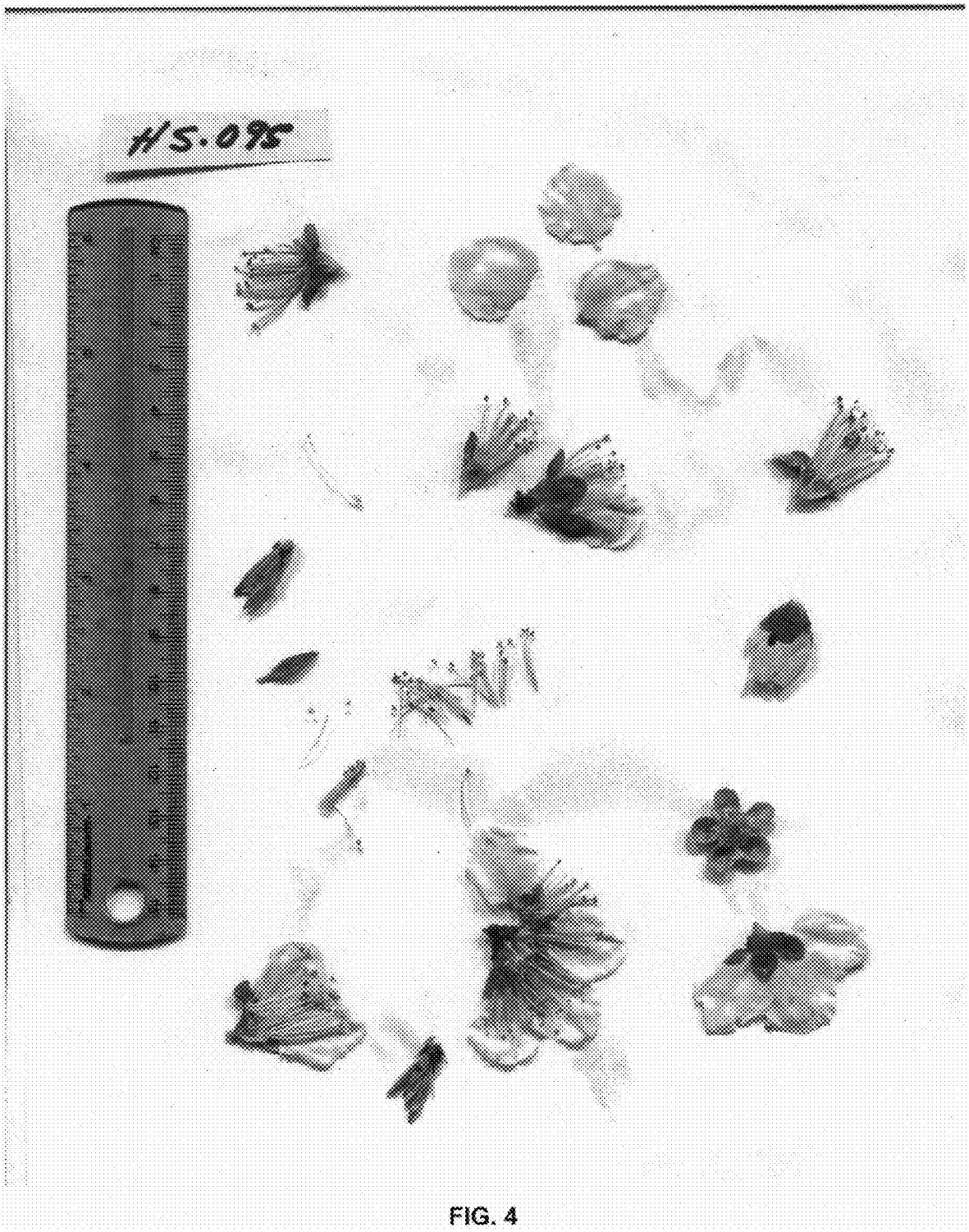
FIG. 4 is a color photograph of flowers from a fifth leaf year tree.

The colors in these photographs are as nearly true as is reasonably possible in a color representation of this type. Due to chemical development, processing and printing, the fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. § 112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any purpose, or non-infringement which is directed, in whole, or in part, to the present variety.

DETAILED DESCRIPTION

Referring more specifically to the pomological details of this new and distinct variety of nectarine tree, the following has been observed during the tenth fruiting season, and under the ecological conditions prevailing at the orchards of the assignee which are located near the town of Fowler, county of Fresno, state of Calif. All major color code designations are by reference to The R.H.S. Colour Chart (Royal Horticultural Society, Fourth Edition, 2001) provided by The Royal Horticultural Society of Great Britain. Common color names are also occasionally used.

Tree:

*Size*.—Generally considered medium to medium-large in its growth pattern as compared to other common commercial nectarine cultivars ripening in the late season of maturity. The tree of the present variety was pruned to a height of about 270.0 cm. to about 310.0 cm. at commercial maturity. Fruit size can vary with crop load and the conditions under which the fruit and tree are grown.

*Width*.—Approximately 265.0 cm.

*Vigor*.—Considered moderately vigorous. The present nectarine tree variety grew from about 175.0 cm. to about 180.0 cm. in height during the first growing season. The new variety was pruned to a height of approximately 150.0 cm. during the first dormant season, and primary scaffolds were then selected for the desired tree structure.

*Productivity*.—Productive. Fruit set varies from more than the desired crop load, to levels higher than desired amounts, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

*Fruit bearing*.—Regular. Fruit set has been more than adequate during the previous years of observation, and thinning was necessary during the past 8 years on both the original seedling and on subsequent asexually reproduced trees.

*Tree form*.—Upright and pruned into a vase shape.

*Density*.—Considered moderately dense.

*Hardiness*.—The present tree was grown and evaluated in USDA Hardiness Zone 9. The calculated winter chilling requirements of the new tree is approximately 500 hours at a temperature below 7.0 degrees C. The present variety appears to be hardy under typical central San Joaquin Valley climatic conditions.

Trunk:

*Diameter*.—Approximately 22.0 cm in diameter when measured at a distance of approximately 15.5 cm. above the soil level. This measurement was taken at the beginning of the 8th growing season.

*Bark texture*.—Considered moderately rough, with folds of papery scarfskin being present. Since bark development and coloration change with advancing tree age this characteristic varies with the tree vigor, age and regional conditions. Therefore, this is not a dependable descriptor of the new variety.

*Lenticels*.—Numerous flat, oval lenticels are present. The lenticels range in size from about 4.0 millimeters to about 6.0 mm. in width, and between about 1.0 and about 2.5 millimeters in height. The development and size of the trunk lenticels can be influenced, to some degree, by the ambient growing conditions, and are not, necessarily, a dependable characteristic of this variety. As trees of this variety mature, lenticels are present, but they are generally covered by increasing layers of cork (mature bark) and therefore become less apparent.

*Lenticel color.*—Considered an orange brown (RHS Greyed-Orange Group 165 B).

*Bark coloration.*—Variable, but it is generally considered to be a greyed tan (RHS Greyed-White Group 157 B). This bark description was taken from trees in their tenth leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

Branches:

*Size.*—Considered medium large for the variety.

*Diameter.*—Average as compared to other nectarine varieties. The branches have a diameter of about 13.0 centimeters when measured during the 8th year after grafting.

*Flowering shoot thickness.*—Average for the species. Generally, the most consistent flower bud development and therefore potential fruiting sites occur on shoots which are approximately 7.0 millimeters in diameter or larger but generally less than approximately 15.0 millimeters in diameter at the time of bloom.

*Surface texture.*—Average and appearing relatively smooth but with more furrowing on wood which is several years old.

*Crotch angles.*—Primary branches are considered variable and are usually growing at an angle of about 45 degrees when measured from a horizontal plane.

*Current season shoots.*—Surface texture — Substantially glabrous.

*Internode length.*—Approximately 3.0 cm.

*Color of mature branches.*—Approximately Grey brown (RHS Greyed-Orange Group 177 A).

*Current season's shoots.*—Color. — Light green (RHS Yellow-Green Group 145 B). The color of new shoot tips is considered a bright and shiny green (RHS Yellow-Green Group 146 D). The vegetative shoot color can be significantly influenced by plant nutrition, irrigation practices, and exposure to sunlight, and therefore should not be considered a consistent botanical characteristic of this new variety.

Leaves:

*Size.*—Considered somewhat elongated and narrow for the species. Leaf measurements have been taken from vigorous, upright, current-season growth, at approximately mid-shoot. The leaf size is often influenced by prevailing growing conditions, quality and intensity of available sunlight, and the location of the leaf within the tree canopy. For this reason, leaves sizes can vary significantly based upon the ambient light and other cultural factors listed above and are not typically considered a dependable botanical descriptor.

*Leaf length.*—Approximately 155.0 to approximately 180.0 millimeters (including the petiole).

*Leaf width.*—Approximately 35.0 to approximately 48.0 millimeters.

*Leaf base-shape.*—The leaves generally exhibit equal marginal symmetry relative to the leaf longitudinal axis.

*Leaf form.*—Lanceolate.

*Leaf tip form.*—Acuminate.

*Leaf color.*—Upper Leaf Surface — Medium green (approximately RHS Green Group 137 C).

*Leaf texture.*—

*Upper leaf surface.*—Glabrous.

*Lower leaf surface.*—Glabrous.

*Leaf color.*—Lower Leaf Surface — Medium green (approximately RHS Green Group 138 B).

*Leaf venation.*—Pinnately veined.

*Mid-vein.*—Color — Considered a pale green (approximately RHS Yellow-Green Group 145 D).

*Leaf margins.*—Gently undulating.

*Form.*—Considered crenulate.

*Uniformity.*—Generally uniform.

*Leaf petioles.*—

*Form.*—Considered canaliculated and having a more pronounced trough when viewed from the dorsal aspect. The petiole margin is considered rounded when viewed from the ventral aspect.

*Size.*—Considered medium-small for the species.

*Length.*—About 6.0 to about 9.0 mm.

*Diameter.*—About 1.5 to about 2.0 mm.

*Color.*—A yellowed green (approximately RHS Yellow-Green Group 146 D).

*Texture.*—Glabrous.

*Strength.*—Durable for species until senescence.

*Leaf glands.*—

*Size.*—Considered relatively small for the species; about 2.0 mm. in width; and about 2.0 mm. in height.

*Number.*—Generally, one and less common two glands appear per marginal side are found. Observations of more than two glands per marginal side are very uncommon.

*Type.*—Glands located at the base of the leaf are predominantly reniform in shape. An additional one to two, or occasionally more glands, which appear reniform, and stalked, gland primordia are often present at the basal margin of the leaf petiole as well.

*Color.*—Considered a yellowed greed, approximately (RHS Yellow-Green Group 151 A). Typically, the coloration of the glands darkens, and occasionally begins to desiccate relatively early in the growing season.

*Leaf stipules.*—

*Size.*—Typically, the stipule is approximately 9.0 mm to approximately 12.0 mm in length and approximately 1.0 mm in width.

*Number.*—Typically, 2 per leaf bud, and up to 6 per shoot tip.

*Form.*—Lanceolate in form and having a serrated marginal edge.

*Color.*—Green (approximately RHS Yellow-Green Group 145 A) when young, but graduating to a brown color (approximately RHS Greyed-Orange Group 165 A) with advancing senescence. The leaf stipules are generally considered to be early deciduous.

Flower buds:

*Hardiness.*—No winter injury (bud death) has been noted during the last several years of observation in the central San Joaquin Valley. The new variety of nectarine tree has not been intentionally subjected to drought, cold or heat stress, and therefore this information is not available.

*Flower bud*.—Size — Variable, and dependent on the state of maturity. The flower buds as described were observed approximately 7 days prior to bloom.
*Length*.—Approximately 16.5 millimeters.
*Diameter*.—Approximately 9.5 millimeters.
*Surface texture*.—Pubescent.
*Orientation*.—Considered appressed but appear less so as the blossoms near opening.
*Bud scale color*.—Approximately RHS Greyed-Orange Group 175 A.

Flowers:
*Date of first bloom*.—Observed on Feb. 21, 2018.
*Blooming time*.—Considered average to slightly early mid-bloom in relative comparison to other commercial nectarine cultivars grown in the central San Joaquin Valley. The date of full bloom was observed on Feb. 28, 2018. The date of full bloom varies slightly with climatic conditions, and prevailing cultural practices.
*Duration of bloom*.—Approximately 8 or more days. This characteristic varies slightly with the prevailing climatic conditions.
*Flower class*.—Considered a perfect flower, complete and perigynous.
*Flower type*.—The variety is considered to have a showy type flower.
*Flower size*.—Considered large. The flower diameter at full bloom, is approximately 35.0 to approximately 42.0 millimeters.
*Bloom quantity*.—Considered abundant.
*Flower bud density*.—Generally considered dense.
*Flower bud frequency*.—Generally, two flower buds appear per node, occasionally one flower bud per node is observed. Very rarely three floral Bud's per node are observed.
*Petal size*.—Generally considered large for the species.
*Petal length*.—Approximately 18.0 to approximately 20.0 millimeters.
*Petal width*.—Approximately 11.0 to approximately 14.0 millimeters.
*Petal form*.—Considered broadly ovate.
*Petal count*.—Nearly always 5.
*Petal texture*.—
*Upper petal texture*.—Very finely pubescent, satin like.
*Lower petal texture*.—Very finely pubescent, satin like.
*Petal color*.—Considered a light pink at the popcorn stage (RHS Red-Purple Group 62 D) and darkening with advanced senescence, and the exposure of sunlight, to a medium-dark pink (RHS Red-Purple 63 C). This darkening of the petal is generally most present within the margins of the petal claw.
*Fragrance*.—Slight.
*Petal claw*.—
*Form*.—The claw is considered ovate and is generally large.
*Length*.—Approximately 12.0 millimeters.
*Width*.—Approximately 10.0 millimeters.
*Petal margins*.—Generally, slightly undulate.
*Petal apex*.—Entire.
*Flower pedicel*.—
*Length*.—Considered medium with an approximate length of about 1.0 to about 2.0 millimeters.
*Diameter*.—Approximately 1.0 to approximately 1.5 millimeters.
*Color*.—A medium brown, approximately (RHS Grey-Brown Group N199 D) depending on pedicel and fruit maturity and timing of visual observance.
*Strength*.—Tenacious. Average for the species.
*Texture*.—Generally smooth to slightly undulate.
*Floral nectaries*.—
*Color*.—Considered a a pale yellow (approximately RHS Greyed-Yellow Group 160 A).
*Calyx*.—
*Surface texture*.—Generally glabrous.
*Color*.—Approximately RHS Greyed-Purple Group 183 B.
*Sepals*.—
*Upper surface texture*.—Moderately pubescent.
*Lower surface texture*.—Glabrous.
*Number*.—5 sepals.
*Size*.—Considered medium.
*Sepal length*.—Approximately 4.0 to approximately 6.0 millimeters.
*Sepal width*.—Approximately 4.5 to approximately 6.0 millimeters.
*Sepal shape*.—Generally obovate.
*Sepal margin*.—Considered smooth and entire.
*Sepal color*.—Approximately RHS Greyed-Purple Group 183 A.
*Anthers*.—
*Generally*.—Average in size, having a length of approximately 2.0 mm to approximately 2.5 mm, a width of approximately 1.5 mm to approximately 2.0 mm, and a depth of approximately 1.0 mm to approximately 1.5 mm.
*Color*.—Yellow when viewed dorsally and prior to dehiscence (approximately RHS Yellow-Orange Group 20 A).
*Position relative to stigma*.—Generally, the stigma is superior to the anthers by approximately 1.0 to approximately 2.0 millimeters.
*Pollen production*.—Pollen is abundant and has a yellow color (approximately RHS Yellow-Orange Group 20 A).
*Fertility*.—Self-fertile.
*Filaments*.—
*Size*.—Approximately 14.0 to approximately 17.0 millimeters in length.
*Color*.—Considered white to a pinkish-white (RHS White Group N155 D).
*Pistil*.—
*Number*.—Usually one, and only rarely more than one.
*Generally*.—Considered medium in size.
*Length*.—Approximately 17.0 to approximately 19.0 millimeters in length including the ovary.
*Ovary*.—Glabrous in texture and drupe in shape.
*Color*.—Considered a very pale green (approximately RHS Yellow-Green Group 150 D).
*Surface texture*.—The variety has a long glabrous pistil.
*Position relative to petals*.—At flower maturity the stamens grow to be superior to the petals.

Fruit:
*Maturity when described*.—Firm ripe condition (shipping ripe).
*Date of first picking*.—Approximately Jun. 20, 2018.

*Date of last picking*.—Jun. 29, 2017. The date of harvest can vary with the prevailing climatic conditions, crop loads and the current climatic and cultural practices.

*Size*.—Generally — Considered medium large.

*Average cheek diameter*.—Approximately 75.0 to approximately 80.0 millimeters.

*Average axial diameter*.—Approximately 74.0 to approximately 79.0 millimeters.

*Typical weight*.—Approximately 257.0 grams. The fruit size and weight can vary and are dependent on the prevailing cultural practices, growing conditions and therefore is not particularly distinctive of the new variety.

*Fruit form*.—Generally — Considered globose. The fruit is generally very uniform in symmetry.

*Mucron tip*.—Absent.

*Fruit suture*.—No stitching exists along the suture line.

*Suture*.—Color — Generally, the fruit appears blushed to the same degree as the skin (approximately RHS Orange-Red Group 34 A).

*Ventral surface*.—Form — Considered even, and uniform in appearance, when it is viewed from the lateral, sutural plane.

*Apex*.—Shape — Rounded to slightly retuse.

*Base*.—Shape — Generally rounded to slightly retuse.

*Stem cavity*.—Generally — It extends in a rounded circular form which is generally considered uniform. The stem cavity is rounded but slightly extended toward the suture. The average depth of the stem cavity is about 8.0 to about 10.0 mm. The average width of the stem cavity is about 26.0 mm. The average length of the stem cavity, when measured in the suturial plane is about 45.0 mm.

*Fruit skin*.—

*Thickness*.—Considered medium in thickness, and tenacious to the flesh.

*Surface texture*.—Glabrous.

*Taste*.—Non-astringent.

*Tendency to crack*.—Not observed in the previous years of observation and evaluation.

*Fruit skin color*.—

*Blush color*.—Generally speaking, a red blush exists on a majority of the skin of the fruit (approximately RHS Orange-Red Group 34 A), and is more typically present on the portions of the fruit facing the sunlight. The blush of the fruit typically covers approximately 85% to approximately 95% of the fruit skin surface. The percentage of the blush on the fruit skin surface can vary, and is generally dependent upon the fruit's exposure to direct sunlight; specific fruit maturity; and also the prevailing ecological and cultural conditions under which the fruit was grown.

*Ground color*.—A medium white (approximately RHS. White Group 155 C). The ground color of the fruit can vary significantly based upon the maturity of the fruit when this measurement is taken and generally gains a lighter and less green cast with higher maturity.

*Fruit glossiness*.—Fruit is considered to have a medium glossiness.

*Fruit stem*.—

*Size*.—Medium in length, approximately 6.0 to approximately 8.0 millimeters.

*Diameter*.—Approximately 2.0 to approximately 3.0 millimeters.

*Color*.—Pale yellow-green (approximately RHS Yellow-Green Group N144 C).

*Fruit flesh*.—

*Ripening*.—Considered even.

*Texture*.—Firm, crunchy, juicy and dense. Considered non-melting in flesh classification.

*Lenticels*.—Generally very weekly expressed and found toward the base of the fruit. Fruit exposed to increased sunlight tend to exhibit more conspicuous lenticels.

*Fibers*.—Present but not prominent.

*Aroma*.—Slight.

*Eating quality*.—Considered very good.

*Flavor*.—Considered balanced with sweetness and acidity.

*Juice production*.—Moderate.

*Brix*.—About 14.0 to about 19.5 degrees. This characteristic varies slightly with the number of fruits per tree; fruit position on the tree; the maturity of fruit when harvested; the prevailing cultural practices; and the ambient climatic conditions.

*Acidity*.—Considered medium. Approximately 0.4 titratable acidity at fruit harvest. Acid levels assayed from fruit flesh can vary with fruit maturity, length of time in cold storage, sunlight exposure, and climatic, regional, seasonal and cultural influences.

*Flesh color*.—It is considered white (approximately RHS White Group 155 A). The flesh color nearest to the stone can exhibit very small amounts of red bleed (approximately RHS Red Group 53B) radiating from the stone.

Stone:

*Type*.—Considered a tight freestone.

*Size*.—It is generally considered to be medium for the species. The stone size varies significantly depending upon the tree vigor, the crop load, and the prevailing growing and cultural conditions under which the tree was grown.

*Length*.—Average, about 30.0 to about 35.0 millimeters.

*Width*.—Average, about 23.0 to about 27.0 millimeters.

*Diameter*.—Average, about 17.0 to about 20.0 millimeters.

*Form*.—Roughly ovoid.

*Stone base*.—Shape — The stone is considered shortly attenuate.

*Apex*.—Shape — The stone exhibits a slight acute apex.

*Stone surface*.—

*Surface texture*.—Considered irregularly furrowed toward the apex. Further, more pitting exists in the mid-portion of the stone (laterally) and is more common toward the base.

*Ridges*.—Ridging is generally more prominent, and is usually oriented parallel, and laterally relative at the ventral and dorsal margins.

*Ventral edge*.—The ventral edge is generally is described as having adjoining ridges formed from each hemisphere. There are longitudinal grooves running alongside this joined ventral suture. Secondarily there can exist an additional set of parallel ridges, one on each side of the major ridge. These secondary ridges are less prominent and do not always extend from the hilum to the apex.

*Dorsal edge*.—Shape — Generally considered even. The folds of the surface ridges appearing on the external margins often end gently along the suture.

*Stone color*.—The color of a mature, dry stone is generally considered a dull brown, approximately (RHS Greyed-Purple Group 183 B). Stone color can vary considering how recently the fruit has ripened, harvested, degree of oxidation, surface drying and blanching due to exposure sunlight.

*Tendency to split*.—Splitting has rarely been noted.

*Kernel*.—

*Length*.—Approximately 16.0 to approximately 19.0 millimeters.

*Width*.—Approximately 12.0 to approximately 15.0 millimeters.

*Thickness*.—Approximately 4.0 to approximately 6.0 millimeters.

*Size*.—The kernel is considered medium in size.

*Form*.—Considered generally ovoid.

*Kernel surface texture*.—Kernel pellicle is shortly pubescent.

*Color*.—A dark tan (RHS Greyed-Orange Group 165 C).

*Use*.—The present variety 'Wanectone' is considered to be a nectarine tree of the late season of maturity, and which produces fruit which are considered to be firm, attractively colored, and which are useful for both local and long distance shipping.

*Keeping quality*.—Appears excellent. The fruit of the present variety has stored well for periods of up to 30 days after harvest at 1.0 degree Celsius.

*Shipping quality*.—Good. The fruit of the new nectarine tree variety showed minimal bruising of the flesh or skin damage after being subjected to normal harvesting and packing procedures.

*Resistance to insects and disease*.—No susceptibilities were noted. The present variety has not been intentionally tested to expose or detect any susceptibilities or resistances to any known plant, fruit diseases, insect, frost, winter injury or other environmental factors.

Although the new variety of nectarine tree possesses the described characteristics when grown under the ecological conditions prevailing near Fowler, Calif., in the Central part of the San Joaquin Valley of California, variations of the usual magnitude, and characteristics incident to changes in growing conditions, fertilization, nutrition, pruning, pest control, frost, climatic variables and changes in horticultural management are to be expected.

Having thus described and illustrated our new variety of nectarine tree, what we claim is new, and desire to secure by plant Letters Patent is:

1. A new distinct variety of nectarine tree substantially as illustrated and described, and which is characterized principally as to novelty by producing an attractively colored white-fleshed, freestone nectarine which is mature for harvesting and shipment approximately June 20 to June 29 under the ecological conditions prevailing in the San Joaquin Valley of central California.

* * * * *